United States Patent [19]

Gras et al.

[11] Patent Number: 5,633,336
[45] Date of Patent: May 27, 1997

[54] POLYAMINES CONTAINING UREA GROUPS AND PROCESS FOR THEIR PREPARATION

[75] Inventors: Rainer Gras, Bochum; Elmar Wolf, Recklinghausen, both of Germany

[73] Assignee: Huels Aktiengesellschaft, Marl, Germany

[21] Appl. No.: 554,569

[22] Filed: Nov. 6, 1995

[30] Foreign Application Priority Data

Nov. 4, 1994 [DE] Germany ............... 44 39 421.7

[51] Int. Cl.$^6$ ............... C08G 18/32
[52] U.S. Cl. ............... 528/68; 528/73; 560/344; 560/345
[58] Field of Search ............... 560/344, 345; 528/68, 73

[56] References Cited

U.S. PATENT DOCUMENTS

| | | | |
|---|---|---|---|
| 4,920,173 | 4/1990 | Gras | 524/590 |
| 4,925,974 | 5/1990 | Gras | 560/336 |
| 5,386,053 | 1/1995 | Otterbach et al. | 560/344 |

FOREIGN PATENT DOCUMENTS

| | | |
|---|---|---|
| 0620212 | 10/1994 | European Pat. Off. . |
| 2308015 | 9/1974 | Germany . |
| 2609995 | 9/1977 | Germany . |
| 2654745 | 6/1978 | Germany . |

*Primary Examiner*—Terressa Mosley
*Attorney, Agent, or Firm*—Oblon, Spivak, McClelland, Maier & Neustadt, P.C.

[57] ABSTRACT

Low-viscosity (cyclo)-aliphatic polyamines containing urea groups and having more than two amino groups may be prepared by reacting (cyclo)aliphatic diamines with polyisocyanates containing isocyanurate groups or biuret groups. Such polyamines are useful as components in PUR reaction finishes and coating and adhesive compositions.

11 Claims, No Drawings

POLYAMINES CONTAINING UREA GROUPS AND PROCESS FOR THEIR PREPARATION

BACKGROUND OF THE INVENTION

1. Field of the Invention

The present invention relates to low-viscosity (cyclo) aliphatic polyamines containing urea groups and having more than 2 amino groups and to a process for their preparation.

2. Discussion of the Background

Low molecular weight (cyclo)aliphatic diamines containing urea groups, and of course particularly higher functional polyamines, are either solid or highly viscous at room temperature and cannot be processed in the absence of a solvent.

However, low-viscosity (cyclo)aliphatic polyamines containing urea groups would be desirable for use in polyurethane (PUR) reaction finishes and also as components in coatings and adhesives. Thus, there is a need for low-viscosity (cyclo)aliphatic polyamines containing urea groups.

SUMMARY OF THE INVENTION

Accordingly, it is one object of the present invention to provide novel polyamines.

It is another object of the present invention to provide novel polyamines which contain urea groups and have a low viscosity.

It is another object of the present invention to provide a process for preparing such polyamines.

It is another object of the present invention to provide novel coating compositions which comprise such a polyamine.

It is another object of the present invention to provide a method for coating a substrate with such a coating composition.

It is another object of the present invention to provide novel adhesives which contain such a polyamine.

It is another object of the present invention to provide a method for adhering two surfaces with such an adhesive.

These and other objects, which will become apparent during the following detailed description, have been achieved by the inventors' discovery that low-viscosity (cyclo)aliphatic polyamines containing urea groups may be obtained by reacting (cyclo)aliphatic diamines with polyisocyanates containing isocyanurate groups or biuret groups.

The present invention thus provides to low-viscosity (cyclo)aliphatic polyamines containing urea groups and having more than two amino groups, obtainable by reacting diamines of the formula (I)

$$R^1\text{—NH—A—NH—}R^2 \quad (I)$$

where A represents a (cyclo)aliphatic hydrocarbon radical having 2–16C atoms which is optionally $C_{1-4}$-alkyl-substituted, $R^1$ and $R^2$ denote H or a radical of the formula

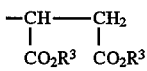

and R3 denotes a (cyclo)aliphatic hydrocarbon radical having 1–12C atoms, which is optionally branched, with polyisocyanates containing isocyanurate and/or biuret groups of the formula (IIa) and (IIb)

$$\text{OCN—(B)—}[X]_n\text{—NCO} \quad (IIa)$$

and $$\text{OCN—(B)—NCO}, \quad (IIb),$$

where B denotes

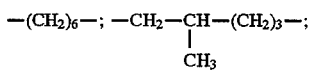

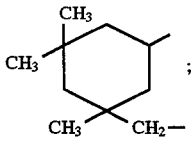

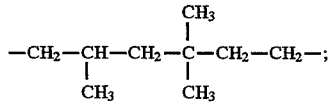

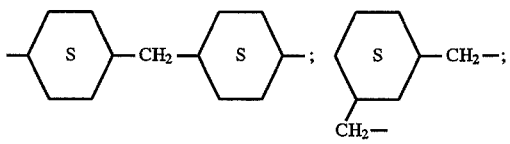

$[X]_n$ denotes:

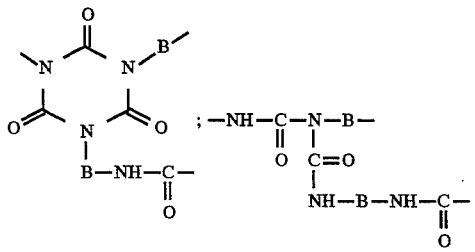

and n denotes 1–4 and S indicates a saturated ring, the weight ratio of (IIa) to (IIb) is (100 to 20) to (0 to 80) and 1 to 5 mole of the diamine (I) are used per the total of NCO groups in the compounds of formulae (IIa) and (IIb).

The invention furthermore provides low-viscosity (cyclo) aliphatic polyamines containing urea groups and having more than two amino groups, obtainable by:

(A) reacting diamines of the formula (I)

$$NH_2\text{—A—}NH_2 \quad (I)$$

where A represents a (cyclo)aliphatic hydrocarbon radical having 2–16C atoms which is optionally $C_{1-4}$-alkyl-substituted, with polyisocyanates containing isocyanurate and/or biuret groups and of the formula (IIa) and (IIb)

OCN—(B)—[X]$_n$—NCO     (IIa)

and

OCN—(B)—NCO     (IIb), where B denotes

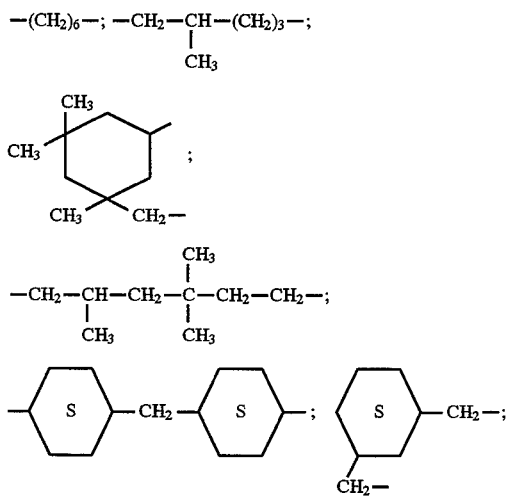

[X]$_n$ denotes:

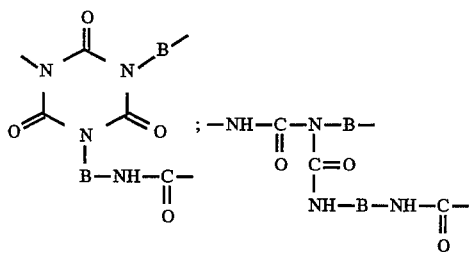

and n denotes 1–4, the weight ratio of (IIa) to (IIb) is (100 to 20) to (0 to 80) and 1 to 5 mole of the diamines (I) are used per the total of NCO groups in the compounds of formulae (IIa) and (IIb); and (B) and then reacting the product with one mole of maleic or fumaric $C_{1-2}$-(cyclo)aliphatic hydrocarbyl ester per $NH_2$ equivalent.

The invention also provides low-viscosity, ureacontaining (cyclo)aliphatic polyamines, which contain inert compounds, such as, for example, plasticizers, in amounts of 5 to 100 parts by weight, based on the weight of the diamine of formula (I).

DETAILED DESCRIPTION OF THE PREFERRED EMBODIMENTS

Thus, thee low-viscosity (cyclo)aliphatic polyamines containing urea groups according to the present invention can be obtained by various processes.

In a first method, when $R^1$ and $R^2$ are hydrogen or a radical of the formula —CH(COR$^3$)CH$_2$CO$_2$R$^3$, the preparation of the compounds according to the present invention is carried out by reacting the compounds of formulae (I) and (II) in a molar ratio of 1:1 to 5:1, the polyisocyanate of formula (II) being added in portions to the diamine of formula (I) which is heated to 100°–190° C., with thorough stirring and blanketing with nitrogen. After the end of the polyisocyanate addition, the reaction mixture is heated for about a further 10 minutes. It is then cooled to room temperature.

In a second method for the preparation of the polyamines according to the present invention, the polyamines produced by the first method in which $R^1$ and $R^2$ are hydrogen are reacted as follows. The reaction mixture is cooled to room temperature and is reacted with a maleic or fumaric $C_{1-2}$-(cyclo)aliphatic hydrocarboyl ester so that 1 mole of maleic or fumaric ester is reacted per 1 $NH_2$ equivalent at 50° to 70° C.

The compounds according to the present invention—the reaction products of the compounds of formulae (I) and (II)—are characterized by an amine content of 1–4 mmol/g, by an isocyanurate group content of 1–6 % (based on 126 g/mol) or by a biuret group content of 1–5 % (based on 98 g/mol). Their viscosity at 25° C. can be varied within a wide range. It is 100–10$^5$ mPa.s, depending on the ratio of NH equivalents to NCO equivalents.

The diamines of formula (I) used for the preparation of the polyamines according to the present invention have long been known and do not form a subject of the present invention. They are obtained by reacting the diamines $H_2N$—A—$NH_2$ and maleic or fumaric esters, 0.5 mole of diamine being reacted in a known manner per mole of maleic or fumaric ester. The diamines $H_2N$—A—$NH_2$ are aliphatic or cycloaliphatic diamines, such as, for example, 1,6-diaminohexane, 2-methyl-1,5-diaminopentane 2,2,4(2,4,4)-trimethyl-1,6 diaminohexane (TMD), 2,4'- and/or 4,4'-diaminodicyclohexylmethane, 1,11-diaminoundecane, 1,12-diaminododecane, 1,4- and 1,2-diaminocyclohexane, m-hexahydroxylylenediamine, 1-amino-3,5,5-trimethyl-5-aminomethylcyclohexane (isophoronediamine, abbreviated to IPD).

The polyisocyanates which are suitable for the preparation of the polyamines according to the present invention are polyisocyanates containing isocyanurate or biuret groups. The preparation of these isocyanuratoisocyanates is described in German Offenlegungsschrift 23 25 826, 26 44 684, 28 21 109 and 29 16 301. They are prepared by partial trimerization of the diisocyanate with the aid of a catalyst—the quaternary ammonium salts described in German Offenlegungsschrift 29 16 201 have proved most suitable—and subsequent separation of the unconverted diisocyanate by thin-film distillation from the reaction product, the polyisocyanate containing isocyanurate groups. As a rule, the monomer-freed isocyanuratoisocyanates are used for the reaction of the diamines with the isocyanuratoisocyanates by the process according to the invention. In some cases, it has proved expedient to use the partially trimerized diisocyanate mixture without separating the unconverted diisocyanate beforehand. The polyisocyanates which contain biuret groups and are suitable according to the invention are described in German Offenlegungsschrift 23 08 015. They are prepared by reacting water with excess diisocyanate, the unconverted diisocyanate being separated by thin film distillation after biuret formation is complete. The same applies here as in the case of the polyisocyanates containing isocyanurate groups. As a rule, the monomer-freed polyisocyanate containing biuret groups is used; in some cases, however, removal of diisocyanate may be dispensed with.

The compounds according to the invention are outstandingly suitable for the preparation of PUR reaction finishes, coatings and adhesives, the curing of which is effected at room temperature or slightly elevated temperature, as a rule 80° C. The coatings and adhesives of the present invention will typically contain, in addition to the polyamine of the present invention, a curing agent such as hydroxy-functional polyesters and acrylic resins. PUR coatings are described in Kirk-Othmer, *Encyclopedia of Chemical Technology*, 4th Ed., Wiley, N.Y., vol. 6, pp. 686–690 (1993), which is incorporated herein by reference.

Other features of the invention will become apparent in the course of the following descriptions of exemplary embodiments which are given for illustration of the invention and are not intended to be limiting thereof.

EXAMPLES

A.1. Reaction Products of 1 Mole of Diamine and 2 Moles of Maleic Ester

General Preparation Method 1 mole of diamine is added dropwise to 2 moles of maleic or fumaric ester at 50°–60° C. in such a way that the temperature of the reaction mixture does not exceed 70° C. After the end of the diamine addition, heating is continued for about a further 2 hours at 60° C. to complete the reaction. A further treatment (distillation) of the reaction mixture is not required for the further reaction with the polyisocyanate.

A.2. Polyisocyanates

Polyisocyanate 1

Commercial isocyanuratoisocyanate based on isophorone diisocyanate having an NCO content of 17.2%.

Polyisocyanate 2

Commercial isocyanuratoisocyanate based on hexamethylene diisocyanate having an NCO content of 21%.

Polyisocyanate 3

Commercial biuret based on hexamethylene diisocyanate having an NCO content of 22.9%.

B.1. Examples 1 to 11

Compounds According to the Invention (Reaction: A.1.+A.2.)

General Preparation Method

The polyisocyanate is added in portions, in the course of about 0.5 hour, to the disecondary diamine heated to 100° to 150° C., with thorough stirring and blanketing with nitrogen. After the end of the polyisocyanate addition, the mixture is immediately cooled to room temperature.

TABLE 1

| No. | Composition Diamine (1 mol) | Maleic ester (2 mol) | NH$_2$ mmol/g | Viscosity at 25° C. mPa · s |
|---|---|---|---|---|
| 1 | IDP | Diethyl maleate | 3.77 | 340 |
| 2 | IDP | Dibutyl maleate | 3.12 | 165 |
| 3 | IDP | Di-2-ethylhexyl maleate | 2.26 | 126 |
| 4 | TMD | Diethyl maleate | 3.89 | 100 |
| 5 | TMD | Dibutyl maleate | 3.17 | 95 |
| 6 |  H$_2$N—CH$_2$—⟨S⟩—CH$_2$—NH$_2$ | Diethyl maleate | 4.05 | 870 |
| 7 | 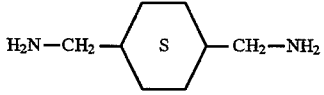 H$_2$N—CH$_2$—⟨S⟩—CH$_2$—NH$_2$ | Dibutyl maleate | 3.28 | 730 |
| 8 | 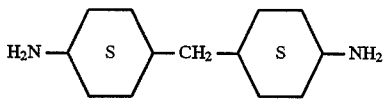 H$_2$N—⟨S⟩—CH$_2$—⟨S⟩—NH$_2$ | Diethyl maleate | 3.56 | 1200 |
| 9 | 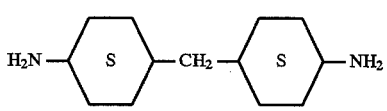 H$_2$N—⟨S⟩—CH$_2$—⟨S⟩—NH$_2$ | Dibutyl maleate | 2.92 | 1080 |

TABLE 2

| Example No. | Composition Parts by wt. | Diamine (A.1.) | Parts by wt. | Polyisocyanate (A.2) | NH:NCO— ratio as number of equivalents | NH₂ content mmol/g | Visc. at 25° mPa · s |
|---|---|---|---|---|---|---|---|
| 1 | 70 | No. 4 | 30 | No. 1 | 2.26:1 | 1.51 | 10,000 |
| 2 | 80 | No. 4 | 20 | No. 2 | 2.18:1 | 2.12 | 16,000 |
| 3 | 90 | No. 4 | 10 | No. 2 | 7.17:1 | 3.02 | 1,300 |
| 4 | 90 | No. 4 | 10 | No. 1 | 8.37:1 | 3.10 | 1,850 |
| 5 | 80 | No. 1 | 20 | No. 2 | 3.11:1 | 2.08 | 21,000 |
| 6 | 90 | No. 1 | 10 | No. 2 | 7:1 | 3.0 | 10,500 |
| 7 | 92.6 | No. 2 | 7.4 | No. 2 | 7.8:1 | 2.4 | 2,780 |
| 8 | 86.3 | No. 2 | 13.7 | No. 2 | 3.89:1 | 1.95 | 16,500 |
| 9 | 90 | No. 5 | 10 | No. 1 | 7.15:1 | 2.46 | 740 |
| 10 | 90 | No. 7 | 10 | No. 1 | 7.3:1 | 2.55 | 1,730 |
| 11 | 90 | No. 9 | 10 | No. 1 | 6.59:1 | 2.35 | 1,700 |

B.2. Examples 12 to 25

Compounds According to the Invention (Reaction Products of Diamines and Polyisocyanates (A.2.))

General Preparation Method

The polyisocyanate is added in portions, with thorough stirring and blanketing with nitrogen, to the diamine heated to 150°–180° C., in a manner such that the temperature of the reaction mixture does not exceed 190° C. After the end of the polyisocyanate addition, heating is continued for about a further 10 minutes. The reaction is then complete.

TABLE 3

| Example No. | Composition Parts by wt. | Diamine | Parts by wt. | Polyisocyanate | NH₂ content mmol/g | Viscosity at 25° C. mPa · s |
|---|---|---|---|---|---|---|
| 12 | 500 | IPD | 100 | Polyisocyanate 1 | 9.15 | 920 |
| 13 | 500 | IPD | 125 | Polyisocyanate 1 | 8.32 | 3,200 |
| 14 | 500 | IPD | 150 | Polyisocyanate 1 | 7.60 | 23,700 |
| 15 | 500 | TMD | 100 | Polyisocyanate 1 | 9.61 | 43 |
| 16 | 500 | TMD | 150 | Polyisocyanate 1 | 8.31 | 180 |
| 17 | 500 | TMD | 200 | Polyisocyanate 1 | 7.48 | 1,130 |
| 18 | 500 | TMD | 250 | Polyisocyanate 1 | 6.71 | 5,900 |
| 19 | 500 | IPD | 100 | Polyisocyanate 1 | 8.01 | 4,650 |
| 20 | 500 | IPD | 125 | Polyisocyanate 1 | 7.80 | 11,500 |
| 21 | 500 | H₂N—⟨S⟩—NH₂ | 100 | Polyisocyanate 1 | 13.5 | 100 |
| 22 | 500 | (cyclohexane with S, NH₂, NH₂) | 200 | Polyisocyanate 1 | 11.18 | 100 |
| 23 | 500 | (cyclohexane with S, NH₂, NH₂) | 300 | Polyisocyanate 1 | 9.27 | 870 |
| 24 | 500 | (cyclohexane with S, NH₂, NH₂) | 400 | Polyisocyanate 1 | 7.77 | 26,000 |
| 25 | 500 | IPD | 160 | Polyisocyanate 2 | 7.38 | 39,000 |

B.3. Examples 26 to 31

Compounds According to the Invention

(Reaction Products of B.2.+Maleic Ester)

General Preparation Method

The preparation of the compounds according to the invention is carried out analogously to the preparation of the compounds described in A.1., 1 amine equivalent of the amines B.2. being reacted per mole of maleic or fumaric ester.

TABLE 4

| Example No. | Parts by wt. | Polyamine Example No. (B.2.) | Parts by wt. | Maleic ester | $NH_2$ content mmol/g | Viscosity at 25° C. mPa · s |
|---|---|---|---|---|---|---|
| 26 | 133.6 | 6 | 172 | Diethyl maleate | 3.27 | 1,100 |
| 27 | 120 | 16 | 172 | Diethyl maleate | 3.42 | 900 |
| 28 | 120 | 16 | 228 | Dibutyl maleate | 2.87 | 400 |
| 29 | 132 | 14 | 228 | Dibutyl maleate | 2.78 | 1,200 |
| 30 | 132 | 14 | 172 | Diethyl maleate | 3.29 | 7,500 |
| 31 | 132 | 24 | 228 | Dibutyl maleate | 2.80 | 480 |

The present application is based on German Patent Application P 44 39 421.7 filed on Nov. 4, 1995, which is incorporated herein by reference in its entirety.

Obviously, numerous modifications and variations of the present invention are possible in light of the above teachings. It is therefore to be understood that, within the scope of the appended claims, the invention may be practiced otherwise than as specifically described herein.

What is claimed as new and is desired to be secured by Letters Patent of the United States is:

1. A low-viscosity (cyclo)aliphatic polyamine containing urea groups and having more than two amino groups, obtained by reacting a diamine of the formula (I):

$$R^1—NH—A—NH—R^2 \quad (I)$$

wherein A is a (cyclo)aliphatic hydrocarbon radical having 2–16 carbon atoms which is optionally $C_{1-4}$-alkyl-substituted, $R^1$ and $R^2$ are H or a radical of the formula

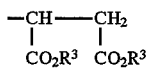

wherein $R^3$ is a (cyclo)aliphatic hydrocarbon radical having 1–12 carbon atoms, which is optionally branched, with polyisocyanates containing isocyanurate and/or biuret groups and of the formula (II):

$$OCN—(B)—[X]_n—NCO \quad (IIa)$$

and $$OCN—(B)—NCO \quad (IIb),$$

wherein B is

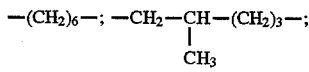

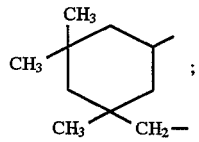

-continued

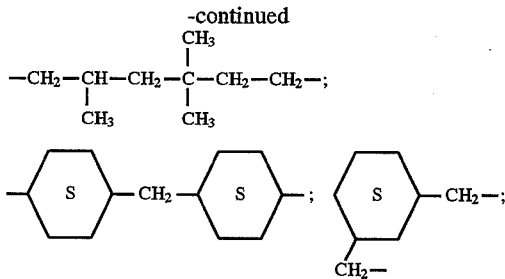

$[X]_n$ is:

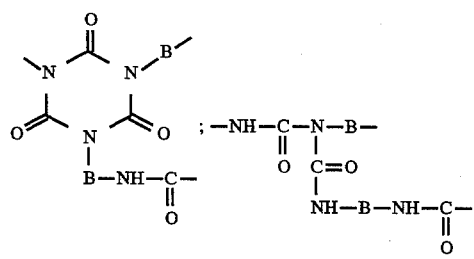

and n is 1–4, the weight ratio of (IIa) to (IIb) is (100 to 20) to (0 to 80) and 1 to 5 moles of the diamine (I) are reacted per the total moles of NCO groups in the compounds of formulae (IIa) and (IIb).

2. The polyamine according to claim 1, which contains 0.01 to 5 parts by weight of an inert compound.

3. The polyamine according to claim 2, which contains a plasticizer.

4. A low-viscosity (cyclo)aliphatic polyamine containing urea groups and having more than two amino groups, obtained by:

(A) reacting a diamine of the formula (I):

$$NH_2—A—NH_2 \quad (I)$$

wherein A is a (cyclo)aliphatic hydrocarbon radical having 2–16 carbon atoms which is optionally $C_{1-4}$-alkyl-substituted, with polyisocyanates containing isocyanurate and/or biuret groups and of the formula (II):

OCN—(B)—[X]$_n$—NCO  (IIa)

and

OCN—(B)—NCO  (IIb), wherein B is

—(CH$_2$)$_6$—; —CH$_2$—CH—(CH$_2$)$_3$—;
              |
              CH$_3$

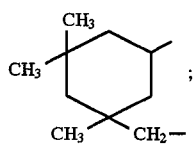

—CH$_2$—CH—CH$_2$—C—CH$_2$—CH$_2$—;
       |       |
       CH$_3$   CH$_3$
       (with CH$_3$ above C)

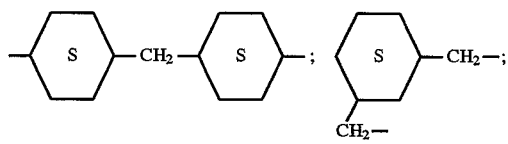

[X]$_n$ denotes:

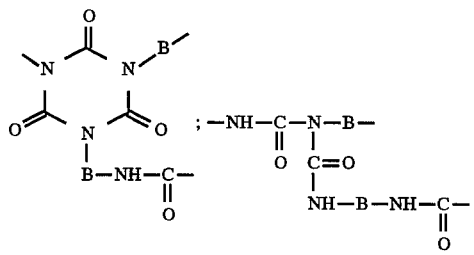

and n is 1–4, the weight ratio of (IIa) to (IIb) is (100 to 20) to (0 to 80) and 1 to 5 moles of the diamine (I) are reacted per the total of NCO groups in the compounds of formulae (IIa) and (IIb); and (B) reacting the product with one mole of maleic or fumaric $C_{1-12}$-(cyclo)aliphatic hydrocarbyl ester per NH$_2$ equivalent.

5. The polyamine according to claim 4, which contains 0.01 to 5 parts by weight of an inert compound.

6. The polyamine according to claim 5, which contains a plasticizer.

7. A process for the preparation of a low-viscosity (cyclo)aliphatic polyamine containing urea groups, said process comprising:

reacting a diamine of formula (I):

R$^1$—NH—A—NH—R$^2$  (I)

wherein A is a (cyclo)aliphatic hydrocarbon radical having 2–16 carbon atoms which is optionally $C_{1-4}$-alkyl-substituted and R$^1$ and R$^2$ are H or a radical of the formula

—CH——CH$_2$
  |     |
  CO$_2$R$^3$  CO$_2$R$^3$ wherein R$^3$ is a (cyclo)aliphatic hydrocarbon radical having 1–12 carbon atoms, which is optionally branched, with polyisocyanates containing isocyanurate and/or biuret groups of formulae (IIa) and (IIb):

OCN—(B)—[X]$_n$—NCO  (IIa)

and

OCN'(B)—NCO  (IIb), wherein B is

—(CH$_2$)$_6$—; —CH$_2$—CH—(CH$_2$)$_3$—;
              |
              CH$_3$

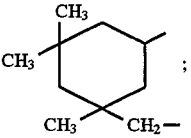

—CH$_2$—CH—CH$_2$—C—CH$_2$—CH$_2$—;
       |       |
       CH$_3$   CH$_3$

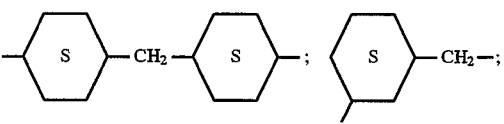

[X]$_n$ is:

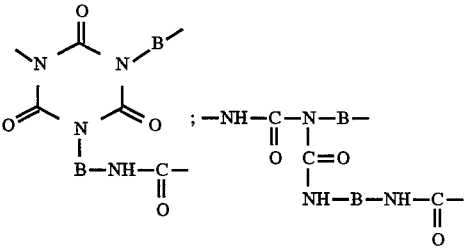

the weight ratio of (IIa) to (IIb) is (100 to 20) to (0 to 80) and 1 to 5 mole of the diamine (I) are reacted per the total of NCO groups in the compounds of formulae (IIa) and (IIb), at a temperature of 100° to 190° C.

8. A process for the preparation of a (cyclo)aliphatic polyamine containing urea groups, said process comprising:

(A) reacting a diamine of formula (I):

H$_2$N—A—NH$_2$  (I)

wherein A is a (cyclo)aliphatic hydrocarbon radical having 2–16 carbon atoms which is optionally $C_{1-4}$-alkyl-substituted, with polyisocyanates containing isocyanurate and/or biuret groups of formulae (IIa) and (IIb):

OCN—(B)—[X]ₙ—NCO  (IIa)

and

OCN—(B)—NCO  (IIb), wherein B is

—(CH₂)₆—; —CH₂—CH(CH₃)—(CH₂)₃—;

[trimethyl cyclohexyl-CH₂— structure];

—CH₂—CH(CH₃)—CH₂—C(CH₃)₂—CH₂—CH₂—;

[dicyclohexylmethane structure]; [cyclohexane with two CH₂— substituents];

$[X]_n$ is:

[isocyanurate ring structure]; —NH—C(O)—N(B—NH—C(O)—NH—B—NH—C(O)—)—B— (biuret structure)

and n is 1–4, the weight ratio of (IIa) to (IIb) is (100 to 20) to (0 to 80) and 1 to 5 mole of the diamine (I) are reacted per the total of NCO groups in the compounds of formulae (IIa) and (IIb), at a temperature of 150°–190° C.; and (B) reacting the product with one mole of maleic or fumaric $C_{1-2}$-(cyclo)aliphatic hydrocarbyl ester per $NH_2$ equivalent at a temperature of 50° to 70° C.

9. A method of coating an article, comprising coating said article with a composition which comprises a low-viscosity (cyclo)aliphatic polyamine containing urea groups and having more than two amino groups, said (cyclo)aliphatic polyamine being obtained by reacting a diamine of the formula (I):

$R^1$—NH—A—NH—$R^2$  (I)

wherein A is a (cyclo)aliphatic hydrocarbon radical having 2–16 carbon atoms which is optionally $C_{1-4}$-alkyl-substituted, $R^1$ and $R^2$ are H or a radical of the formula

—CH(CO₂R³)—CH₂(CO₂R³)

wherein $R^3$ is a (cyclo)aliphatic hydrocarbon radical having 1–12 carbon atoms, which is optionally branched, with polyisocyanates containing isocyanurate and/or biuret groups and of the formula (II):

OCN—(B)—[X]ₙ—NCO  (IIa)

and

OCN—(B)—NCO  (IIb), wherein B is

—(CH₂)₆—; —CH₂—CH(CH₃)—(CH₂)₃—;

[trimethyl cyclohexyl-CH₂— structure];

—CH₂—CH(CH₃)—CH₂—C(CH₃)₂—CH₂—CH₂—;

[dicyclohexylmethane structure]; [cyclohexane with two CH₂— substituents];

$[X]_n$ denotes:

[isocyanurate ring structure]; —NH—C(O)—N(B—NH—C(O)—NH—B—NH—C(O)—)—B— (biuret structure)

and n is 1–4, the weight ratio of (IIa) to (IIb) is (100 to 20) to (0 to 80) and 1 to 5 moles of the diamine (I) are reacted per the total moles of NCO groups in the compounds of formulae (IIa) and (IIb).

10. A method adhering a first surface to a second surface, comprising:

(i) coating said first surface with a low-viscosity (cyclo) aliphatic polyamine containing urea groups and having more than two amino groups, said (cyclo)aliphatic polyamine being obtained by reacting a diamine of the formula (I):

$R^1$—NH—A—NH—$R^2$  (I)

wherein A is a (cyclo)aliphatic hydrocarbon radical having 2–16 carbon atoms which is optionally $C_{1-4}$-alkylsubstituted, $R^1$ and $R^2$ are H or a radical of the formula

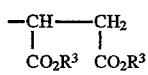

wherein $R^3$ is a (cyclo)aliphatic hydrocarbon radical having 1–12 carbon atoms, which is optionally branched, with polyisocyanates containing isocyanurate and/or biuret groups and of the formula (II):

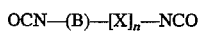 (IIa)

and

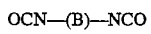 (IIb), wherein B is

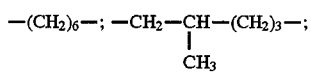

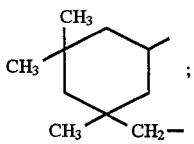

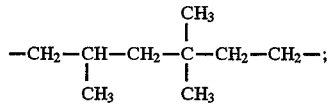

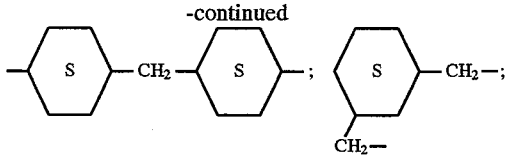

$[X]_n$ denotes:

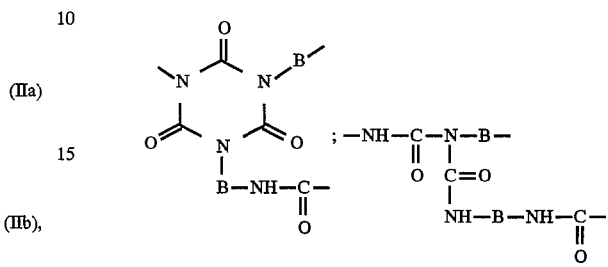

and n is 1–4, the weight ratio of (IIa) to (IIb) is (100 to 20) to (0 to 80) and 1 to 5 moles of the diamine (I) are reacted per the total moles of NCO groups in the compounds of formulae (IIa) and (IIb); and (ii) bring said second surface in contact with said coated first surface.

11. The polyamine according to claim 1, having an amine content of 1–4 mmol/g, an isocyanurate group content of 1–6%, based on 126 g/mol, or a biuret group content of 1–5%, based on 98 g/mol, and a viscosity at 25° C. of 100–$10^5$ mPa.s.

* * * * *